(12) United States Patent
Kondo et al.

(10) Patent No.: US 7,012,681 B2
(45) Date of Patent: Mar. 14, 2006

(54) MAGNETIC TRANSFER APPARATUS AND MAGNETIC RECORDING MEDIUM

(75) Inventors: Masaki Kondo, Osaka (JP); Mitsuo Kobayashi, Kanagawa (JP); Eiichi Fujisawa, Kanagawa (JP)

(73) Assignees: Matsushita Electric Industrial Co., Ltd., Osaka (JP); Fuji Electric Co., Ltd., Kanagawa (JP)

(*) Notice: Subject to any disclaimer, the term of this patent is extended or adjusted under 35 U.S.C. 154(b) by 0 days.

(21) Appl. No.: 10/845,155

(22) Filed: May 14, 2004

(65) Prior Publication Data

US 2004/0263833 A1 Dec. 30, 2004

Related U.S. Application Data

(62) Division of application No. 09/878,924, filed on Jun. 13, 2001, now Pat. No. 6,757,115.

(30) Foreign Application Priority Data

Jun. 13, 2000 (JP) .............................. 2000-177505

(51) Int. Cl.
*G01N 21/00* (2006.01)

(52) U.S. Cl. ................. 356/237.1; 356/237.2

(58) Field of Classification Search .................... None
See application file for complete search history.

(56) References Cited

U.S. PATENT DOCUMENTS

| 5,293,538 | A | * | 3/1994 | Iwata et al. .............. 356/239.1 |
| 5,991,104 | A |   | 11/1999 | Bonyhard |
| 6,031,615 | A | * | 2/2000 | Meeks et al. ............... 356/630 |
| 6,104,681 | A | * | 8/2000 | Yonezawa ................ 369/44.34 |

FOREIGN PATENT DOCUMENTS

| JP | 10-40544 | 2/1998 |
| JP | 11-25455 | 1/1999 |

* cited by examiner

*Primary Examiner*—Michael P. Stafira
(74) *Attorney, Agent, or Firm*—Venable, LLP; Michael A. Sartori (57) ABSTRACT

A magnetic transfer apparatus writing a servo signal by magnetically transferring to a magnetic recording medium, and an optical type inspection apparatus for optically inspecting scratch or foreign matter on the magnetic recording medium wherein a characteristic grease is used for these apparatuses are disclosed. Grease used in the magnetic transfer apparatus or the optical type inspection apparatus generates sulfur type gas in amount less than or equal to 0.5 ppb.

2 Claims, 8 Drawing Sheets

MAGNETIC TRANSFER APPARATUS AND MAGNETIC RECORDING MEDIUM

This application is based on Patent Application No. 2000-177505 filed Jun. 13, 2000 in Japan, the content of which is incorporated hereinto by reference.

BACKGROUND OF THE INVENTION

1. Field of the Invention

The present invention relates generally to a magnetic transfer apparatus for writing a servo signal to a magnetic recording medium by a magnetic transfer technology, and an optical inspection apparatus for inspecting a condition of a surface of the magnetic recording medium, which are particularly featured in greasing agent used in these apparatus. More particularly, the invention relates to a magnetic transfer apparatus, which is featured by a greasing agent used in the apparatus, for writing a positioning servo signal for a data writing/reading head written on a surface of a magnetic recording medium to a magnetic recording medium by a magnetic transfer technology in a hard disk drive employing a magnetic film as a storage material as a currently major trend as external storage device of computers, and an optical inspection apparatus, which is featured by a greasing agent used in the apparatus, for inspecting scratch on the surface of a magnetic recording medium and contaminating condition of before and after magnetic transfer. Also, the present invention relates to a magnetic recording medium to be produced by the magnetic transfer apparatus.

2. Description of the Related Art

In a hard disk drive used as an external storage device of a personal computer, a magnetic head is floated above a surface of a rotating magnetic recording medium by means of a floating mechanism called as slider with maintaining a distance of several tens nanometer for writing and reading data. For example, on the magnetic recording medium, data tracks are arranged concentrically. A magnetic head of a magnetic disk for writing and reading data is moved to a target side on the data track at high speed and is positioned to write bit information on the data track or to read out the already written bit information for writing and reading data.

On the other hand, on the magnetic recording medium, a positioning signal (servo signal) for detecting a relative position between the magnetic head and the data track is written in concentric fashion. The magnetic head performing writing and reading data detects own position at a given interval. For avoiding offset of the center of the servo signal from the center of the magnetic recording medium (or the center of a trace of the magnetic head), the servo signal is written on the medium using a dedicated apparatus called as servo writer after assembling the medium in the hard disk drive. Writing by the servo writer is performed by writing the servo signal to the magnetic recording medium using a servo signal writing head, for example.

On the other hand, the hard disk drive on development reaches a recording density of 20 Gbits/in$^2$. The recording density is increasing at a speed of 60% or more per year. Associating with this, the density of the servo signal for enabling the magnetic head to detect own position is increased to inherently increase writing period by means of the servo writer. Increasing of the writing period by the servo writer should lower productivity of the hard disk drive to cause increasing of the cost.

In order to avoid increasing of the writing period of the servo signal, it has been recently proposed a transfer system for writing the servo signal in a lump by a magnetic transfer apparatus. Development of technology has been performed (for example, Japanese Patent Application Laid-Open No. 10-40544, Japanese Patent Application Laid-Open No. 11-25455). Writing of the servo signal by magnetic transfer, problem may be caused in transfer when scratch or contamination is present on the surf ace of the magnetic recording medium. Therefore, the magnetic recording medium has to be inspected by an optical type inspection apparatus.

In the magnetic transfer apparatus and the optical inspection apparatus, for transporting the magnetic recording medium or performing magnetic transfer and inspection for the magnetic recording medium, various movable portions are present. To the movable portion, a lubricant such as grease is applied. The grease can generate a gas due to friction upon operation of the movable portion or rising of temperature of the overall apparatus. Such gas may deposit on the surface of the magnetic recording medium to adversely affect for magnetic transfer or inspection.

SUMMARY OF THE INVENTION

The present invention has been worked out in view of the problem set forth above. An object of the present invention is to provide a selection method of a grease to be used in a movable portion of the magnetic transfer apparatus or the optical type inspection apparatus, and whereby to provide a magnetic transfer apparatus and an optical type inspection apparatus using such grease.

The first aspect of the present invention relates to a magnetic transfer apparatus for magnetically transferring a servo signal to a magnetic recording medium. The apparatus comprises:

a transfer stage for performing magnetic transfer;

an index portion performing positioning of a magnetic recording medium and supplying said magnetic recording medium to the transfer stage for a magnetic transfer operation;

a transporting portion for transporting the magnetic recording medium to the index portion;

wherein the magnetic transfer apparatus has a plurality of movable portions using a grease; and wherein total amounts of a sulfur type gas generated from the plurality of the movable potions may be less than or equal to 0.5 ppb.

In the magnetic transfer apparatus of the present invention, total amount of the sulfur type gas generated may be preferably less than or equal to 0.35 ppb.

The second aspect of the present invention relates to an optical type inspection apparatus for optically inspecting scratch or foreign matter on a magnetic recording medium. The optical type inspection apparatus comprises:

an optical system for irradiating a light on the magnetic recording medium to inspect a surface of the magnetic recording medium;

an automatic focusing shaft for focusing the optical system;

a transporting portion for transporting the magnetic recording medium to the optical system;

wherein the optical type inspection apparatus has a plurality of movable portions using grease; and wherein total amounts of a sulfur type gas generated from the plurality of the movable potions may be less than or equal to 0.5 ppb.

In the optical type inspection apparatus of the present invention, the total amount of sulfur type gas generated may be less than or equal to 0.35 ppb.

The third aspect of the present invention relates to a magnetic recording medium transferred a servo signal by the magnetic transfer apparatus described in the first aspect of the present invention, comprising at least a magnetic layer, a protective layer and a liquid lubricant layer on a substrate.

The fourth aspect of the present invention relates to a method for manufacturing a magnetic recording medium written a servo signal on a magnetic recording medium being performed by a magnetic transfer apparatus having a plurality of movable portions using a grease which may generate sulfur type gas in amount less than or equal to 0.5 ppb. The method comprises the steps of:

transporting the magnetic recording medium to an index portion for performing magnetic transfer operation;

performing magnetic transfer on a transfer stage for the magnetic recording medium transported to the index portion, thereby to obtain a magnetically transferred magnetic recording medium, and collecting the magnetically transferred magnetic recording medium.

In the method for manufacturing the magnetic recording medium of the present invention, the magnetic transfer apparatus comprises:

a transfer stage for performing magnetic transfer;

an index portion performing positioning of a magnetic recording medium and supplying the magnetic recording medium to the transfer stage for magnetic transfer operation;

a transporting portion for transporting the magnetic recording medium to the index portion;

a plurality of movable portions using grease which may generate sulfur type gas in amount less than or equal to 0.5 ppb.

The method for manufacturing the magnetic recording medium of the present invention, the amount of the sulfur type gas generated may be less than or equal to 0.35 ppb.

Figure 1:
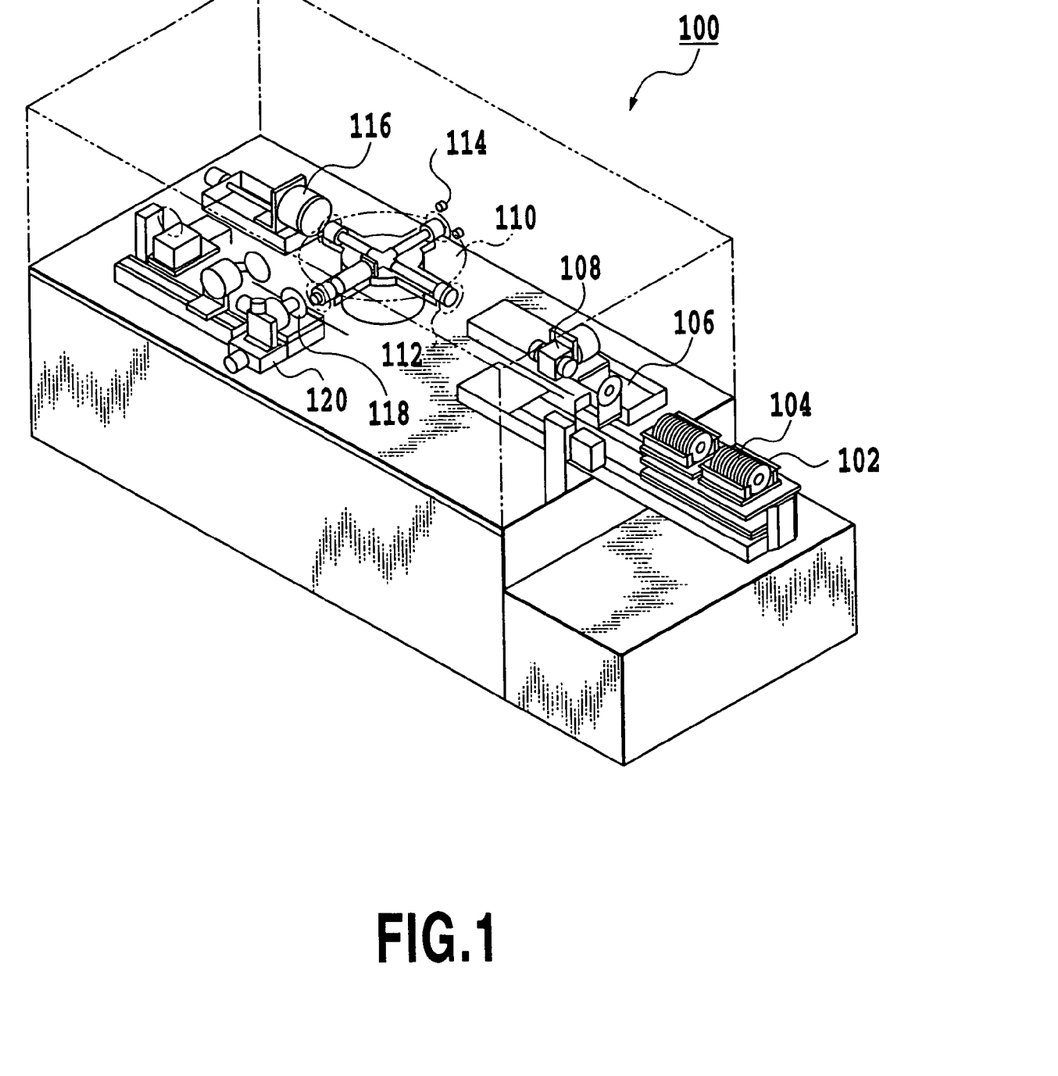
FIG. 1 is a perspective view generally showing a magnetic transfer apparatus.

The magnetic transfer apparatus according to the present invention may be the apparatus shown in FIG. 1, for example, but not limited to the particular construction.

Figure 2:
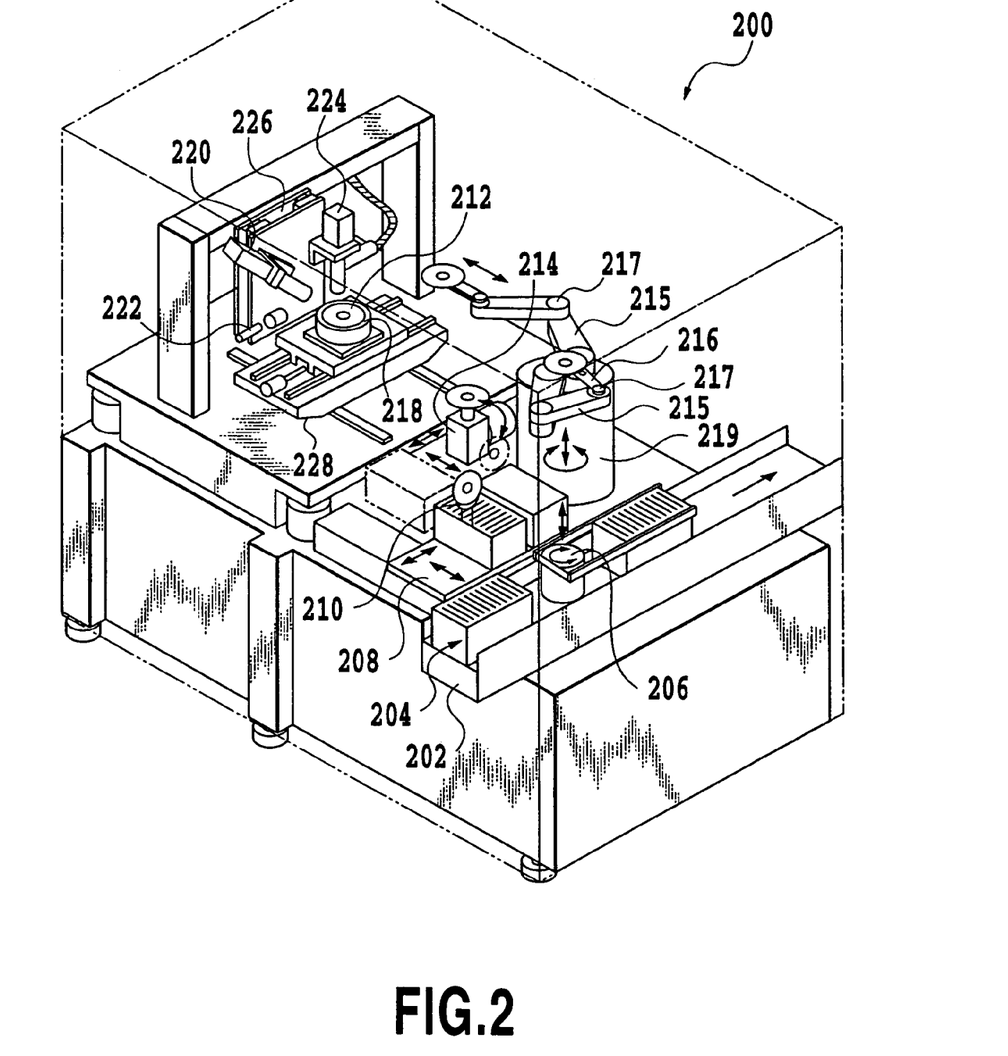
FIG. 2 is a perspective view generally showing an optical type inspection apparatus.

The optical type inspection apparatus according to the present invention may be the apparatus shown in FIG. 2, for example, but not limited to the particular construction.

According to the present invention, by limiting concentration of gas which contains sulfur-containing compounds (hereinafter it refers sulfur type gas) generated from grease used in the magnetic transfer apparatus or the optical type inspection apparatus, the magnetic recording medium processed by such apparatus will not be damaged or corrosion even when it is left in high temperature and high humidity environment, and production of magnetic recording medium can be performed efficiently.

The above and other objects, effects, features and advantages of the present invention will become more apparent from the following description of embodiments thereof taken in conjunction with the accompanying drawings.

BRIEF DESCRIPTION OF THE DRAWINGS

FIGS. 3A and 3B are general illustration showing processes of magnetic transfer to the case of magnetic recording medium, in which

DETAILED DESCRIPTION OF PREFERRED EMBODIMENTS

The present invention will be explained hereinafter in detail.

At first, the first aspect of the present invention will be explained.

The first aspect of the present invention is directed to a magnetic transfer apparatus for recording a servo signal to a magnetic recording medium by magnetic transfer of the servo signal, in which the magnetic transfer apparatus is featured in that a generation amount of a sulfur type gas from a grease used in this apparatus is less than or equal to 0.5 ppb.

Particularly, the magnetic transfer apparatus has a transfer stage performing magnetic transfer, an index portion performing positioning of the magnetic recording medium and performing magnetic transfer operation by supplying the magnetic recording medium to the transfer stage, and a transporting portion for transporting the magnetic recording medium to the index portion for writing the servo signal to the magnetic recording medium by magnetic transfer. The magnetic transfer apparatus has a plurality of movable portions using grease. The generation amount of sulfur type gas generated from grease used in the movable portion is less than or equal to 0.5 ppb.

In general, in the magnetic transfer apparatus or the like, grease is used in the movable portions for smoothing operation of the movable portion. Various types of greases may be used. Most frequently used grease contains sulfur-containing compounds. Such grease generates sulfur-containing compounds as gas due to friction, heat and so on during operation. This gas adversely affects for magnetic transfer.

In the preferred embodiment of the present invention, it is preferred that grease, wherein a concentration of sulfur type gas generated from grease is less than or equal to 0.5 ppb, as analyzed in a manner set out later, is selected. When grease generating sulfur type gas in an amount more than 0.5 ppb in the magnetic transfer apparatus is used in the magnetic transfer apparatus, the obtained magnetic recording medium can cause corrosion at high temperature and high humidity condition.

Figure 7:
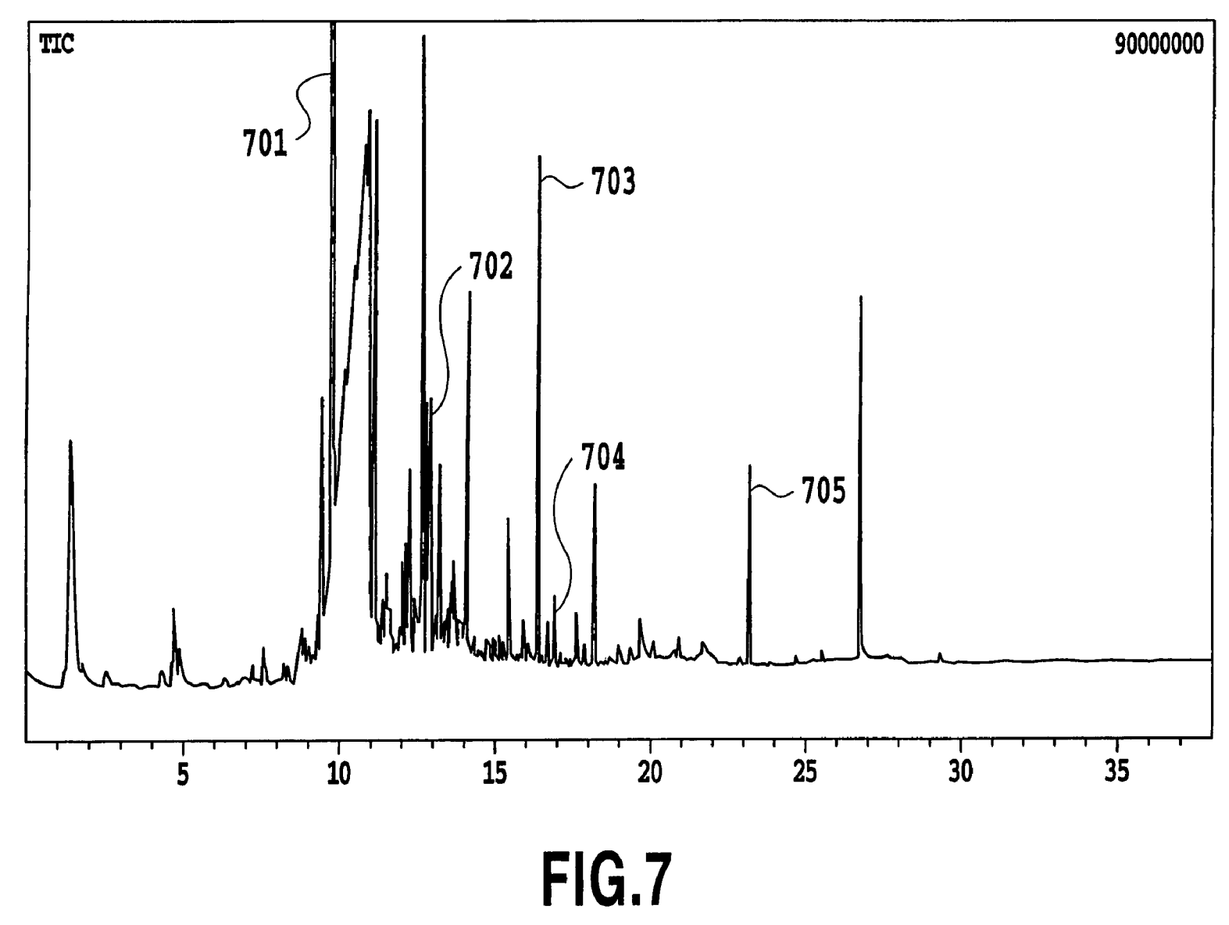
FIG. 7 is a gas chromatographic chart of a grease as analyzed according to the present invention.
Figure 8:
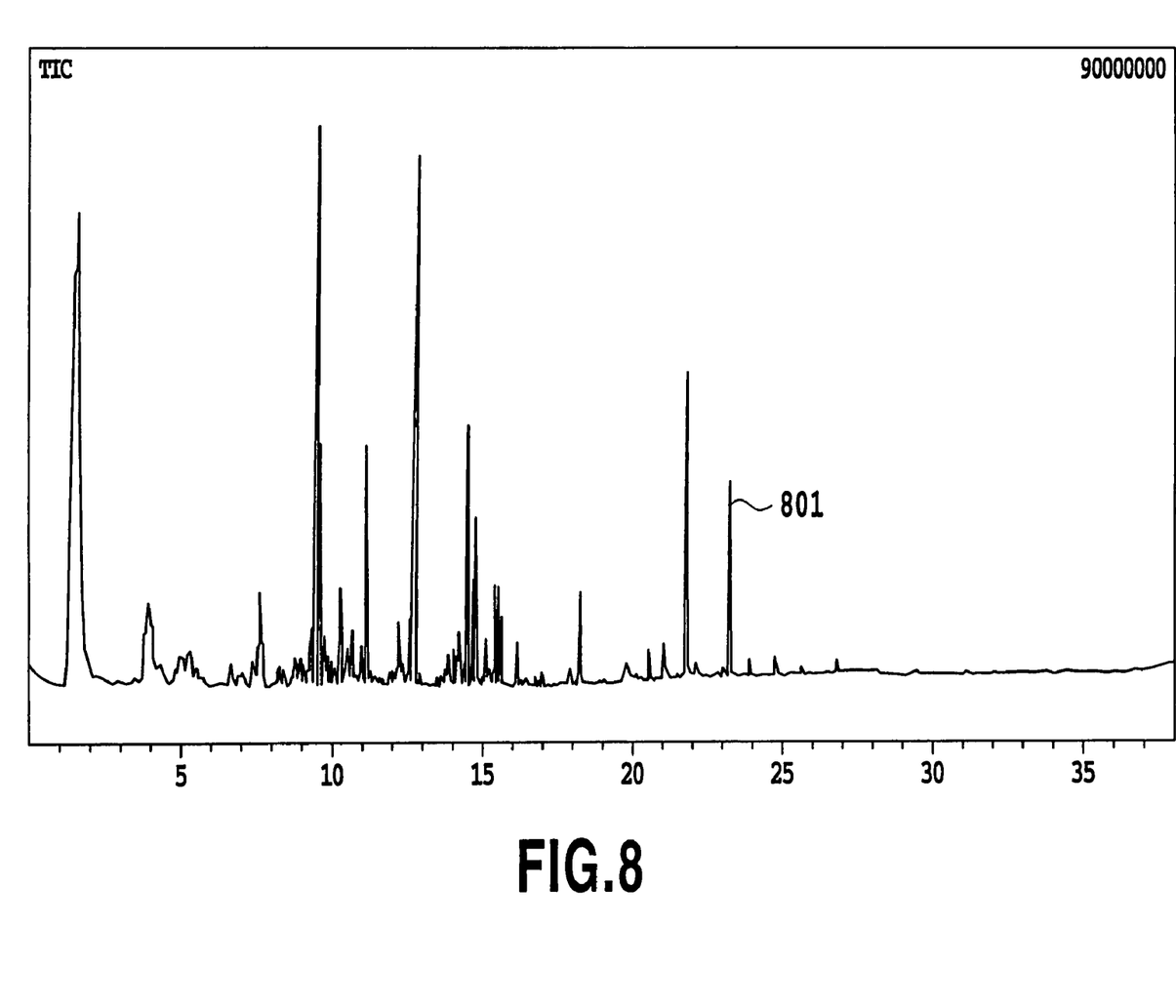
FIG. 8 is a gas chromatographic chart of another grease as analyzed according to the present invention.

In the present invention, a sulfur type gas to be generated from grease includes bis(2-methyl-2-propenyl)sulfide (701: $C_8H_{14}S$, molecular weight: 142), methylthiirane (702; $C_3H_6S$, molecular weight 74), 3,5-bis(1-methylethyl)-1,2,4-trithiolane (703 and 704; $C_8H_{16}S_3$, molecular weight: 208), S-propyl octanethioate (705, $C_{11}H_{22}OS$, molecular weight: 202) and the like may be listed. Chemical formulas of these compounds are as follows:

701
702
703, 704
705, 801

When grease generating these gases is used in the magnetic transfer apparatus according to the present invention, total concentration of these compounds is preferably at less than or equal to 0.5 ppb, more preferable less than or equal to 0.35 ppb.

In the present invention, sulfur type gas containing the compounds set forth above is analyzed and an amount thereof is determined quantitatively by means of the following method to select the grease generating sulfur type gas of the range set forth above.

Analysis of Grease

For grease to be used in the magnetic transfer apparatus and optical type inspection apparatus, the following analysis may be performed.

A sample of grease is applied to a predetermined aluminum plate (e.g. 5×6 mm), and then the sample is analyzed by gas chromatograph mass spectrometer (GC-MASS).

As measuring condition of GC-MASS analysis, for example, sample applied to aluminum plate is headed under the presence of flow of helium. Sulfur type gas generated from grease by heating is trapped. The trapped gas is analyzed by GC-MASS after condensation.

From results of gas chromatography and mass spectrometric analysis, composition and generation amount of sulfur type gas is determined.

Grease useful for the present invention is AFE grease available from THK Kabushiki Kaisha, DEMNUM L65 available from DAIKIN INDUSTRIES, LTD, DEMNUM L100 available from DAIKIN INDUSTRIES, LTD, DEMNUM L200 available from DAIKIN INDUSTRIES, LTD, Grease Z-300, ULVAC JAPAN, LTD, Krytox 240AC, Du Pont Kabushiki Kaisha, Krytox 283AB, Du Pont Kabushiki Kaisha, or the like.

Next, the first aspect of the present invention will be described with reference to FIG. 1. FIG. 1 is a general illustration of the magnetic transfer apparatus which can use grease according to the present invention and shows one example of the present invention. In the following disclosure, the present invention will be explained with reference to FIG. 1, but the magnetic transfer apparatus according to the present invention should not be limited to the one having the shown construction. Grease according to the present invention is used in the movable portion of such apparatus.

For example, the magnetic transfer apparatus shown in FIG. 1 has a cassette stage 102 having a cassette 104, a disk lifter portion 106 lifting the magnetic recording medium, i.e. disk, stored in the cassette, a slave handler 108 transporting the magnetic recording medium, an index portion 110 used for transfer operation, a master handler 118 operating the master disk and a transfer stage 102 performing transfer. The cassette stage 102 having the cassette 104, the disk lifter portion 106 and the slave handler 108 transporting the magnetic recording medium form a transporting portion for transporting the magnetic recording medium. These respective portions have various movable portions, such as rotating mechanism, lifting mechanism and so forth. In these movable portions, grease according to the present invention can be used. In practice, grease of the present invention is used in the cassette moving mechanism, an actuator of the disk lifter portion 106, an actuator of the master handler 118 and so forth.

The magnetic transfer device using the grease according to the present invention will be discussed in greater detail. As well, the magnetic transfer process by the magnetic transfer apparatus will be discussed with reference to FIG. 1.

The magnetic transfer apparatus 100 is constructed with the cassette stage 102, in which the magnetic recording media are housed within the cassette 104, the disk lifter portion 106 lifting up and down the magnetic recording medium in and out the cassette 104, the slave handler 108 transporting the magnetic recording medium from the disk lifter portion to the index portion 110, the index portion 110 performing the magnetic transfer operation in four stages, the master handler 118 and the transfer stage 120 performing transfer.

The magnetic recording medium may be one described later. For example, the magnetic recording medium is a recording medium used in a hard disk drive as external storage device for a computer or the like. However, the present invention is not limited to the recording medium for the hard disk drive. The present invention can be applicable for any magnetic recording media.

The cassette 104 is a container for housing the magnetic recording medium. The cassette 104 has a capability of housing about twenty-five magnetic recording media, such as for hard disk, for example. One or more cassettes 104 can be arranged on cassette stage and can be set in the magnetic transfer apparatus for magnetic transfer.

The disk lifter portion 106 holds the magnetic recording medium for lifting up and down. For example, the disk lifter portion 106 may be formed with a holding mechanism having a semi-circular concave cavity which has a cross-sectionally V-shaped groove extending along the semi-circle of the cavity. On the other hand, the disk lifter portion is arranged within a clearance below the cassette 104 and lifts up and down the magnetic recording medium housed in the cassette 104.

The slave handler 108 is movable between the disk lifter 106 and the index portion 110 and is rotatable in parallel to the moving direction. The slave handler 108 holds the magnetic recording medium to transport from the disk lifer portion 106 to the index portion 110. Accordingly, the slave handler 108 has a mechanism for holding the magnetic recording medium. This mechanism is not particularly limited and is only required to hold a center hole of the magnetic recording medium by holding mechanism such as claws opening and closing by air pressure.

On the other hand, preferably, the slave handler has a pair of holding mechanism in radial alignment in opposition (i.e. the holding mechanism is aligned together at a 180° angle) so that the slave handler 108 can hold both of the magnetic recording medium before magnetic transfer and the magnetic recording medium after magnetic transfer.

The index portion 110 has a construction combining four arms perpendicular to each other and has mechanism for holding the magnetic recording medium at the end of each arm. During one turn of the index portion 110 intermittently, four stages of transfer operation is performed. The transfer operation is constructed by four stages of a waiting stage 112, a slave position measuring stage 114, an initialization stage 116 and transfer stage 120. The magnetic transfer apparatus 100 according to the present invention has a master handler 118, and performs loading and unloading of a master disk used for magnetic transfer.

Next, the magnetic transfer process by the magnetic transfer apparatus of the construction set forth above will be explained.

At first, the magnetic recording medium is upwardly projected from the lower side of the cassette 104 by the disk lifter 106 arranged in the clearance below the cassette stage 102. The magnetic recording medium is held by the slave handler 108 and is transferred to the arm of the index portion 110 waiting at the waiting stage of the index portion.

Here, the magnetic recording medium is transported to the index portion by the slave handler 108. At this time, the magnetic recording medium is not present on the arm side, and is still present on the side of the disk lifter portion 106. Accordingly, before transferring the magnetic recording medium to the arm of the index portion, the slave handler is rotated in parallel to a direction of transporting the magnetic recording medium, and the magnetic recording medium is oriented to disk lifter portion side. Then the magnetic recording medium is transferred to the arm of the disk lifter portion. When the slave handler 108 holds the center hole of the magnetic recording medium by means of the claws opened and closed by air pressure as set forth above and when the arm of the index portion is constructed with the suction head, transferring is performed in the following manner. At first, drawing operation of the air by the suction head is initiated to suck and hold the magnetic recording medium and subsequently transfer the magnetic recording medium to the arm of the index by closing the claws located in the center hole by adjustment of the air pressure.

The magnetic recording medium held in the index portion 110 moves to intermittently rotate per 90° between four stages. At first, at the slave position-measuring stage 114, the center position of the magnetic recording medium sucked and held is measured. According to the result of measurement, the position adjustment is performed so that the master disk may be tightly fitted at the concentrically positioned condition of the magnetic recording medium sucked and held. Next, the initialization stage 116 performs magnetic erasure. The master disk for magnetic transfer in the transfer stage 120 is tightly fitted to the magnetic recording medium to transfer the magnetic pattern onto the medium.

Transfer of the magnetic pattern performed by the magnetic transfer apparatus used in the present invention is performed by using the master disk carrying the servo signal, tightly fitting the master disk and the magnetic recording medium each other, and writing the servo signal on the surface of the magnetic recording medium by a surface recording of magnetic transfer technology. For example, it is possible to use a method to transfer the servo signal for the longitudinal magnetic recording medium using the master disk having uneven shape (i.e. the master disk has concave and convex portion) wherein the convex portions of the uneven shape being formed with ferromagnetic material.

Furthermore, using the magnetic transfer technology employing a perpendicular magnetic recording medium (i.e. the medium in which an orientation of magnetization recorded is the vertical direction on the surface), initialization of the magnetic transfer and transfer are performed.

When transfer is completed, the magnetic recording medium transferred the magnetic pattern (hereinafter occasionally referred to as "transferred magnetic recording medium") is transported to the waiting stage 112 by the arm of the index portion. In the waiting stage 112, the transferred magnetic recording medium by operation opposite to transfer of the magnetic recording medium from the slave handler. 108 to the arm of the index portion is transferred to the slave handler 108.

Upon continuously performing magnetic transfer operation, the slave handler 108 has a pair of holding mechanism in which each holding mechanism is positioned to opposite side each other as set forth above (i.e. each holding mechanism is aligned together at a 180° angle) and thus holds the magnetic recording medium not magnetically transferred the servo signal on the side opposing to the cassette stage 102. After the slave handler 108 receives the transferred magnetic recording medium, the slave handler 108 rotates in parallel to transport direction of the magnetic recording medium to orient the transferred magnetic recording medium toward the cassette stage 102 and to orient the magnetic recording medium before magnetic transfer toward the arm side of the index portion. Subsequently, the magnetic recording medium before magnetic transfer oriented toward the arm side of the index portion is transferred on the arm side of the index portion according to the above mentioned manner. The transferred magnetic recording medium is transported to the disk lifter portion 106 by the slave handler 108. After transporting to the disk lifter portion 106, the disk lifter portion 106 is lowered and the magnetic recording medium houses in the cassette 104.

By repeating the foregoing operation, transfer of the magnetic pattern to the magnetic recording medium is continuously performed by the magnetic transfer apparatus shown in FIG. 1.

It should be noted that the magnetic recording medium is neatly nested with orienting in the predetermined direction so that the side to be magnetically transferred the servo signal may tightly fitted with the master disk.

Figure 3A:
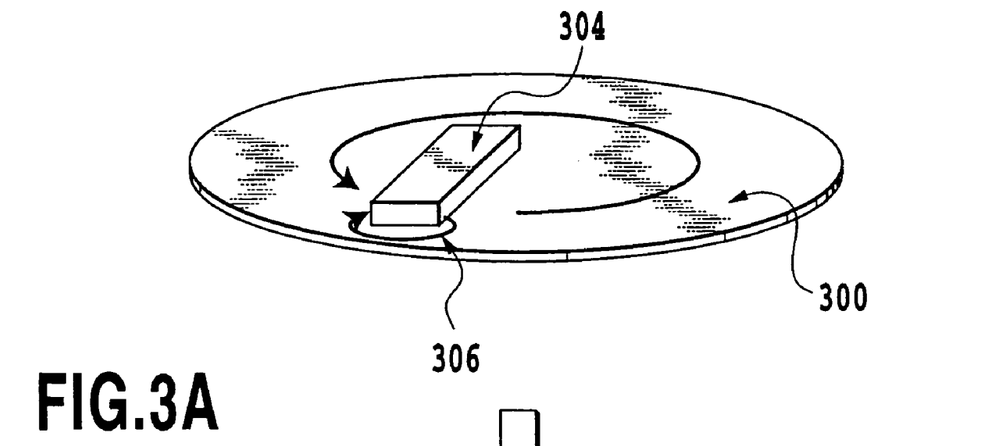
FIG. 3A shows a process of magnetic erasure.
Figure 3B:
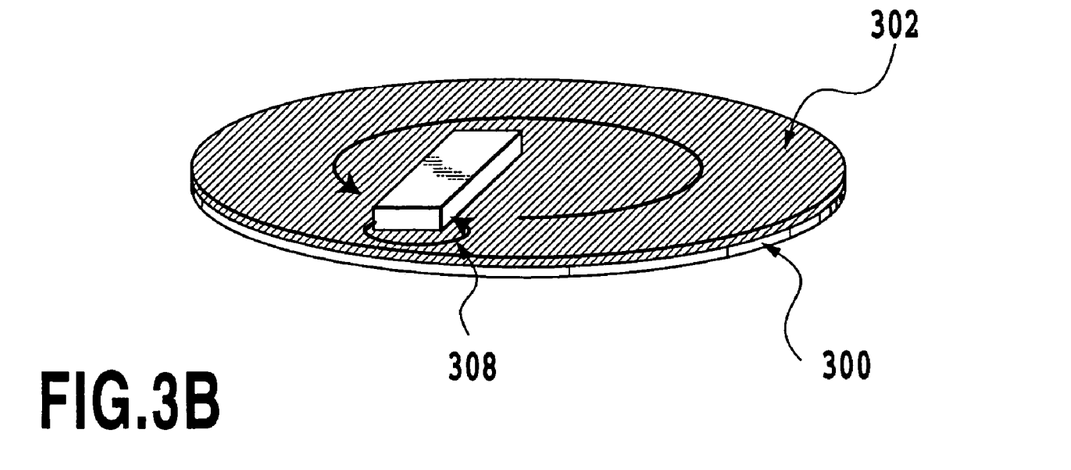
FIG. 3B shows a process of magnetic transfer.

Next, practical process of magnetic transfer to the magnetic recording medium will be explained with reference to FIGS. 3A and 3B.

The magnetic transfer is performed through two stages of magnetic erasure step (the foregoing initialization stage 116) and a step of transferring magnetic pattern (the foregoing transfer stage 120) after tightly fitting the master disk and the magnetic recording medium. FIG. 3A shows magnetic erasure process and FIG. 3B shows magnetic transfer process.

The magnetic erasure is performed by rotating the external magnet 304 for one turn along the surface on the surface of the magnetic recording medium 300. By this, a magnetic field 306 of the external magnet 304 (for example, 0.5 T) erases magnet on the magnetic recording medium.

Transfer of the magnetic pattern is performed by tightly fitting the master disk and the magnetic recording medium and then rotating the external magnet having a magnetic field (e.g. 0.5 T) in a direction opposite to the magnetic erasure is rotated for one turn along the surface of the master disk from the side of the master disk.

Figure 4:
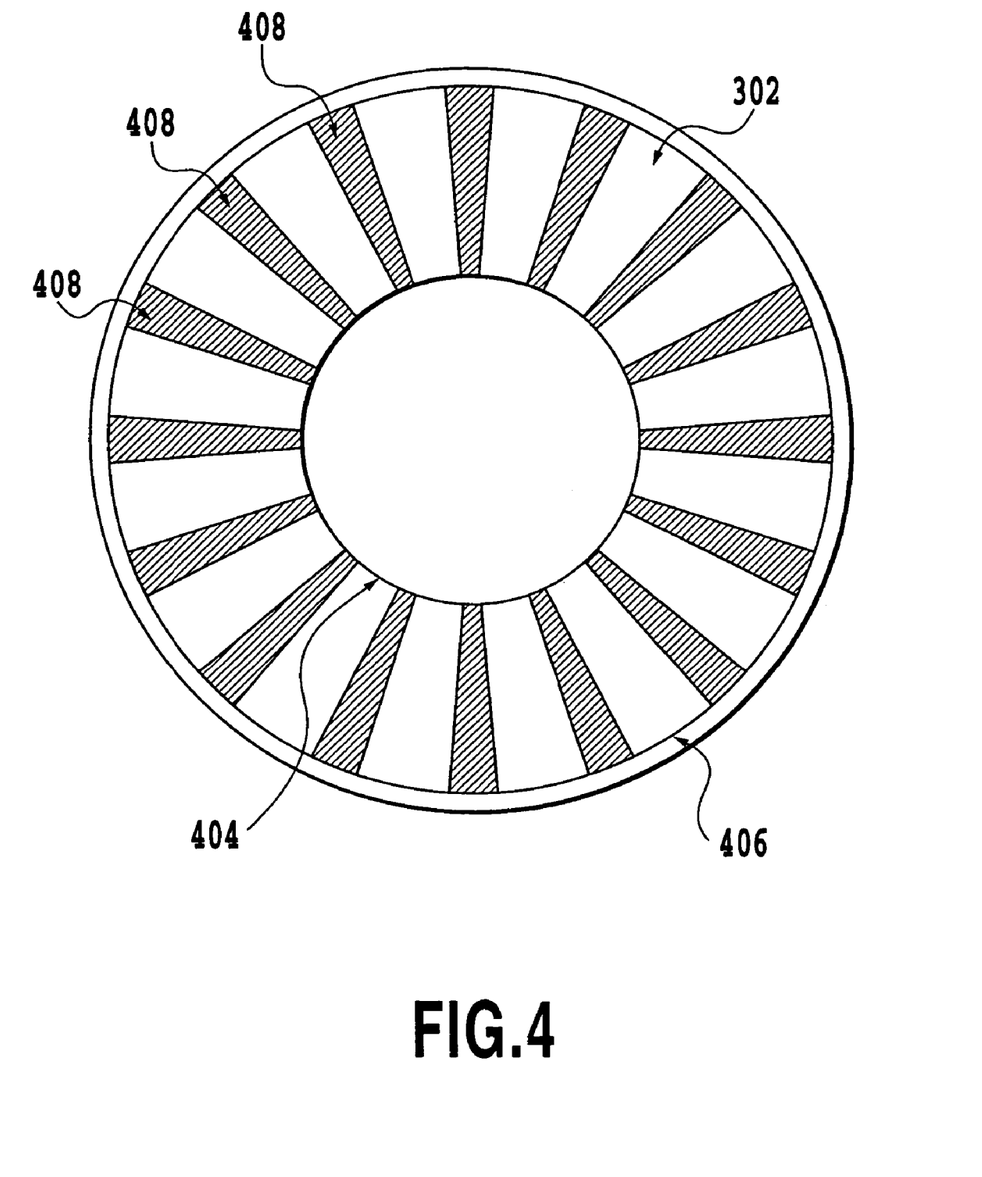
FIG. 4 is a general illustration of a master disk to be used in the magnetic transfer apparatus.

One example of the master disk to be used in the present invention is shown in FIG. 4. A substrate of the master disk is silicon, silicon carbide, aluminum, or the like, for example, while not limitative. A predetermined magnetic transfer pattern (for example, 408 of FIG. 4) is written on the substrate. The transfer pattern is formed through a method that the surface of the substrate is masked by a photolithography, for example, the transfer pattern 408 shown in FIG. 4 is formed by etching, then, a layer of a magnetic material such as cobalt (Co), but not limited to, is formed in the portion of the magnetic transfer pattern 408 by a means such as a vapor deposition, and finally, the mask is removed.

Figure 5:
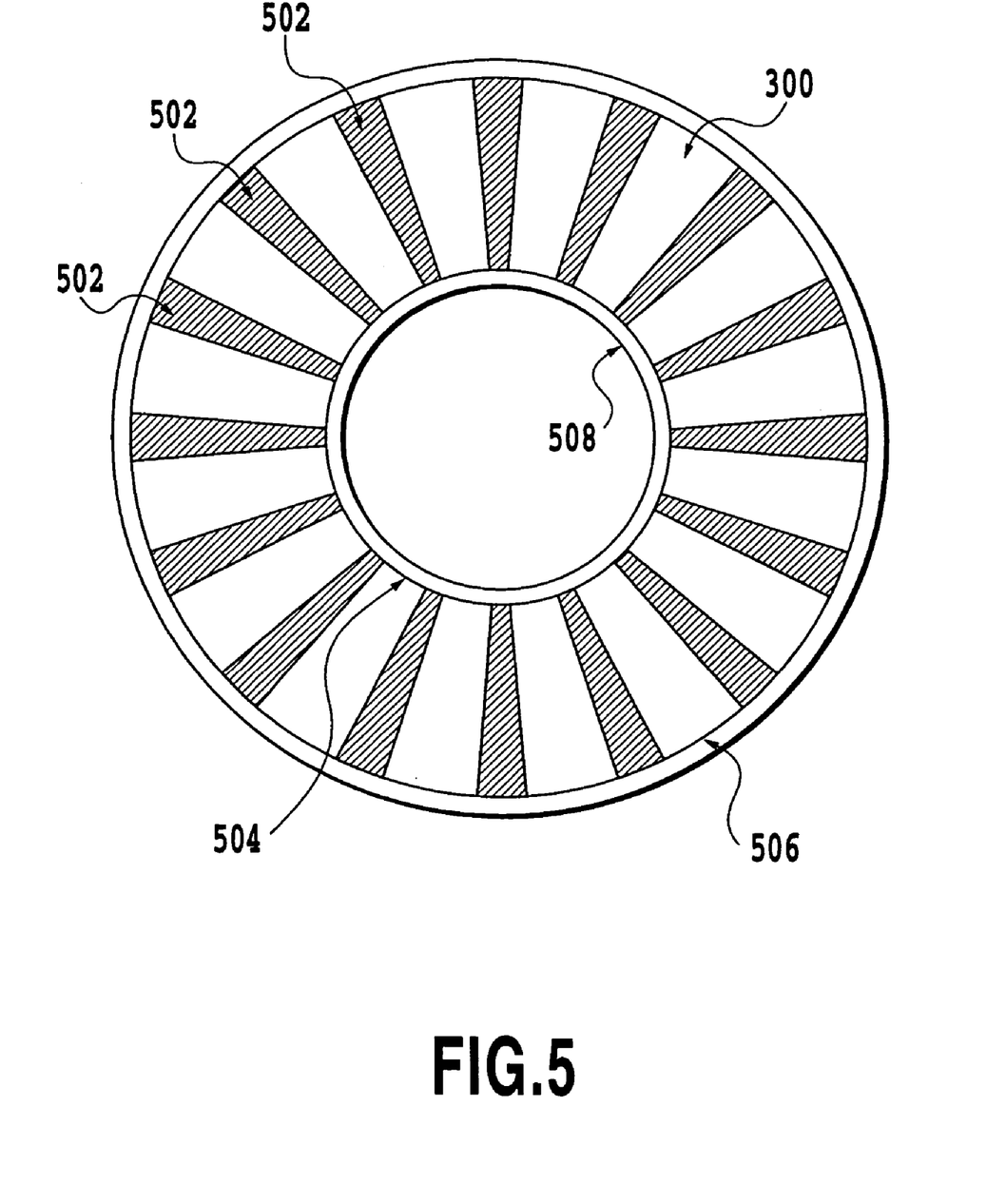
FIG. 5 is a general illustration showing a magnetic recording medium after magnetic transfer.

Such magnetic recording medium magnetically transferred the material transfer pattern (e.g. servo signal) using the master disk becomes the magnetic recording medium 300 having the magnetic transfer pattern (servo signal) shown in FIG. 5. As shown in FIG. 5, the transferred magnetic recording medium 300 has the transferred magnetic pattern region 502 and has an effective innermost diameter (effective innermost diameter 504 of the transferred magnetic pattern) and an outermost diameter (effective outer most diameter 506 of the transferred magnetic pattern). There is no pattern in a portion other than the effective innermost diameter 504 and the effective outer most diameter 506. On the other hand, the magnetic recording medium 300 has a center hole 508. This is fixed by the claws of the holding mechanism of the slave handler 108.

Next, the second aspect of the present invention will be described.

The second aspect of the present invention is directed to an optical type inspection apparatus for optically inspecting scratch or impurity on the magnetic recording medium, in which grease to be used in the optical type inspection apparatus may have a generation amount of sulfur type gas less than or equal to 0.5 ppb.

Particularly, the optical type inspection apparatus includes an optical system for inspecting the surface of the magnetic recording medium by irradiation of light to the magnetic recording medium, an automatic focusing shaft for focusing the optical system and a transporting portion for transporting the magnetic recording medium to the optical system. In the optical type inspection apparatus for optically inspecting scratch or impurity on the magnetic recording medium, there is a plurality of movable portions using grease. Grease used in the movable portions generates sulfur type gas in amount less than or equal to 0.5 ppb.

In general, in the optical type inspection apparatus or the like, grease is used in the movable portion for smoothing operation of the movable portion. Various types of greases may be used. Most frequently used grease contains sulfur-containing compounds. Such grease generates the sulfur type gas (i.e. a gas which contains the sulfur-containing compounds) due to friction, heat and so on during operation. This gas causes adverse affect for the magnetic transfer.

In the present invention, it is preferred that wherein a concentration of sulfur type gas generated from grease is less than or equal to 0.5 ppb, as analyzed in a manner set out later, is selected. In the present invention, total concentration of the sulfur type gas is preferably at less than or equal to 0.5 ppb, more preferable less than or equal to 0.35 ppb.

In practice, grease is one exemplified in the first aspect. In the present invention, when the optical type inspection apparatus uses grease generating sulfur type gas in a concentrated greater than that set forth above for inspecting the magnetic recording medium, corrosion can be caused in the magnetic recording medium corrosion at high temperature and high humidity condition after inspection.

Next, the second aspect of the present invention will be explained with reference to FIG. 2. FIG. 2 is a general illustration of the construction of the optical type inspection apparatus which can use grease according to the present invention. It is one example of the present invention. Hereinafter, the present invention will be explained with reference to FIG. 2. The present invention should not be limited to the optical type inspection apparatus shown in FIG. 2. Grease according to the present invention is used in the movable portion of such apparatus.

For example, the optical type inspection apparatus 200 has an feeding in and feeding out conveyer 202, a cassette transfer device 206 transferring the cassette 204 to the cassette table 208, a disk lifter 210 for lifting up and down a magnetic recording medium 212 housed in the cassette 204, a transfer index 214 for transferring the magnetic recording medium 212 to a handler 216, the handler 216 for transporting the magnetic recording medium to a spindle 218 for inspection, the inspection spindle 218 mounting the magnetic recording medium 212, and the optical system. Among these, the feeding in and feeding out conveyer 202, the cassette transfer device 206, the lifter 210, the transfer index 214, the handler 216 and the inspection spindle 218 constitute a transporting portion.

The optical system has an inspecting optical system 220 that irradiates a light to the magnetic recording medium 212 as an inspection object and a lighting optical system, an observing optical system 224 for observing a light reflected from the magnetic recording medium 212, and the automatic focusing shaft (AF shaft) for focusing the optical system. Each of these portions has various movable portions, such a rotating mechanism, lifting mechanism and so on. In these movable portions, grease according to the present invention is used. More particularly, grease according to the present invention is used in the portion, such as an actuator of the cassette table 208, an actuator of the disk lifter portion 210, a moving mechanism of the inspection stage 228.

The preferred embodiment of the optical inspection apparatus using the grease according to the present invention will be discussed in below. The optical type inspection apparatus and process of inspection of the magnetic recording medium using the optical inspection apparatus will be described with reference to FIG. 2.

The optical type inspection apparatus 200 is constructed with the feeding in and feeding out conveyer 202, the cassette 204, the cassette transfer device 206, the cassette table 208, the disk lifter portion 210, the transfer index 214, the handler 216 having an arm 215 and a connecting portion 217, the inspecting spindle 218, the inspection light optical system 220 that irradiates the light on the magnetic recording medium as inspection object and lighting optical system 222, the observing optical system 224 for observing light reflected from the magnetic recording medium, and the automatic focusing shaft (AF shaft) for focusing the optical system.

The feeding in and feeding out conveyer 202 feeds in the cassette 204 housing the non-inspected magnetic recording medium 212 from the manufacturing line and feeds out the cassette housing the inspected magnetic recording medium 212.

The cassette 204 is a container housing the magnetic recording medium 212. The cassette 204 can house twenty-five magnetic storage media, for example.

The cassette transfer device 206 is a mechanism for transporting the cassette 204 to the cassette table 208. The cassette transfer device 206 has a holder for holding the cassette 204, lifting up and down and rotating the cassette 204, for transferring to the cassette table 208. The cassette transfer device 206 can be designed so as to transfer a plurality of cassette 204 at one time.

The cassette table 208 is a mechanism for setting the cassette 204 housing the magnetic recording medium 212 to the inspection apparatus. One or more cassettes 204 are arranged on the cassette table 208 and thus set in the optical inspection apparatus 200 to perform inspection.

The disk lifter portion 210 holds the magnetic recording medium 212 for lifting in up-and-down direction of the optical type inspection apparatus 200. For example, the lifter 210 has a mechanism for holding the magnetic recording medium 212. The holding mechanism has a semi-circular concave cavity, and a cross-sectionally V-shaped groove extending along the semi-circle of the cavity, for example. On the other hand, the lifter 210 is arranged within a clearance below the cassette 204 for lifting up and down the magnetic recording medium 212 housed within the cassette 104.

The magnetic recording medium 212 is may be one described later. For example, the magnetic recording medium is a recording medium used in a hard disk drive as an external storage device, but not limited to.

The transfer index 214 is a mechanism for transferring the magnetic recording medium 212 held by the lifter 210 to the handler 216. The transfer index 214 can be constructed to rotate the magnetic recording medium 212 held by the lifter 210 in a direction to orient the surface of the magnetic recording medium upwardly as shown in FIG. 2, and to return to the original position by rotating in the reverse direction. On the other hand, the transfer index 214 is constructed with a mechanism like an X-Y stage, and is movable on a surface parallel to the apparatus surface of the optical type inspection apparatus 200 (see FIG. 2). Furthermore, the transfer index 214 has a mechanism for holding the magnetic recording medium 212. This mechanism may be, while not limitative, designed for holding the center hole of the magnetic recording medium by claws opening and closing by air pressure.

The handler 216 holds the magnetic recording medium 212 from a transfer index 214 and transports the magnetic recording medium 212 to the inspecting spindle 218. Accordingly, the handler 216 has a mechanism for holding the magnetic recording medium 212. This mechanism can hold the outer peripheral portion of the magnetic recording medium by the claws, for example. The claws may be moved to open and close by air pressure, for example. In the present invention, the mechanism is not limited to it.

On the other hand, as shown in FIG. 2, the handler 216 may be designed to have two arms 215 for holding both of the magnetic recording medium before inspection and the magnetic recording medium after inspection. The arms 215 can be freely movable in up-and-down direction by a support body 219 supporting the arm. Furthermore, the arm may be rotatable over 360° within a plane parallel to a surface of the inspection spindle 218 mounting the magnetic recording medium 212. On the other hand, as shown in FIG. 2, the arm 215 is constructed with a plurality of portions freely rotating about a connecting portion 217 within a plane parallel to a rotating surface by a plurality of connecting portions. By providing such mechanism, the handler 216 can accurately transport the magnetic recording medium from the transfer index 214 to the inspection spindle 218.

The inspection spindle 218 is a mechanism for mounting and holding the magnetic recording medium 212 to be inspected. The inspection spindle 218 has a suction head, for example, on a surface mounting the magnetic recording medium 212. The suction head may be designed so as to suck an inner periphery portion on the surface of the opposite side to the surface of the magnetic recording medium to be inspected, and so as to hold and fix the magnetic recording medium 212 on the inspection spindle 218. The inspection spindle 218 has a rotating mechanism. Thus, the magnetic recording medium 212 is rotated by the inspection spindle 218.

The inspection light optical system 220 and the lighting optical system 222 are a mechanism for irradiating the inspection light, for example, laser beam to the magnetic recording medium 212 on the inspection spindle 218.

The observing optical system 224 is the optical system for observing the light scattered from the surface of the magnetic recording medium 212 and observing whether a defect due to corrosion or scratch on the magnetic recording medium 212 is present or not.

The AF shaft 226 is a mechanism for automatically adjusting focus of the optical system.

The inspection stage 228 is a mechanism for adjusting the position of the magnetic recording medium 212, such as X-Y stage. On the inspection stage 228, the inspection spindle 218 is arranged.

Next, inspection process of the magnetic recording medium 212 by the optical type inspection apparatus 200 will be explained with reference to FIG. 2.

At first, the cassette 204 housing the magnetic recording media 212 is transported to the feeding in and feeding out conveyer 202 from the production line. This cassette 204 is transferred to the cassette table 208 by the cassette transfer device 206. On the cassette table 208, the magnetic recording medium 212 is projected upwardly from lower side by the lifter 210 arranged within the clearance below the cassette table 208. The magnetic recording medium 212 is held by the transfer index 214. The transfer index 214 has the mechanism for holding the magnetic recording medium 212. This mechanism is may be, but not limited to, the claws opened and closed by air pressure for holding the center hole of the magnetic recording medium.

As shown in FIG. 2, the transfer index 214 can rotate to orient the surface of the magnetic recording medium 212 upwardly, and to return to the original position by rotating in the reverse direction. On the other hand, the transfer index 214 may have a mechanism like an X-Y stage to be movable on the plane parallel to the apparatus plane of the optical type inspection apparatus 200 (see FIG. 2). With such construction, the magnetic recording medium 212 is transported to the position of the handler 216 from the lifter 210. For example, the claw opened and closed by the air pressure such as the claw described above is inserted into the center hole of the magnetic recording medium 212 (i.e. the inner peripheral portion of the magnetic recording medium 212), and is then opened by air pressure to fix the magnetic recording medium 212 on the transfer index 214. Then, the transfer index 214 is rotated over 90° for orienting the magnetic recording medium 212 upwardly to orient the surface of the magnetic recording medium 212 within a rotating plane of the arm 215 of the handler 216. Then, the magnetic recording medium 212 is transferred from the transfer index 214 to the handler 216. For transferring the magnetic recording medium 212 from the transfer index 214 to the handler 216, for example, when the transfer index 214 holds the center hole of the magnetic recording medium by the claws opened and closed by the air pressure and when the handler 216 is designed to hold the outer periphery of the magnetic recording medium by the claws to be actuated by air pressure, transfer of the magnetic recording medium is performed in the following manner. At first, by closing the claws of the handler 216 by adjusting the air pressure thereof, the magnetic recording medium 212 is fixed to the arm 215 of the handler. Next, by adjusting the air pressure of the transfer index 214, the claws in the center hole of the magnetic recording medium is closed to transfer the magnetic recording medium 212 to the arm of the handler.

The magnetic recording medium 212 held on the handler 216 is transported to the inspection spindle 218 by lifting up and down by the support body 219 and rotating operation of the handler 216 (including a rotational movement about the connecting portion 217). Transporting can be performed by rotating the arm 215 in either left or right direction (namely turning the arm clockwise or counterclockwise) in rotating plane. The magnetic recording medium 212 is transferred on the inspection spindle 218 by the handler 216. For transferring, for example, when the handler 216 holds the outer periphery of the magnetic recording medium 212 by the claws opened and closed by air pressure, and when the inspection spindle 218 has the suction head which may be designed so as to suck an inner periphery potion on the surface of the opposite side to the surface of the magnetic recording medium to be inspected, the following operation is performed. At first, the handler 216 is adjusted and the magnetic recording medium 212 is arranged with placing the center thereof in alignment with the center of the inspection spindle 218. Next, by adjusting the air pressure of the handler 216, the claws of the handler is opened to mount the magnetic recording medium 212 on the inspection spindle 218. In conjunction therewith, air drawing operation of the suction head is initiated to suck the magnetic recording medium 212 for fixing. In the optical type inspection apparatus, inspection is performed with rotating the magnetic recording medium 212. Therefore, the center of the magnetic recording medium 212 and the center of the inspection spindle 218 are placed in alignment.

The inspection of the magnetic recording medium 212 is performed by irradiating the light, such as laser beam from the inspection optical system 220 and the lighting optical system 222, and performing scan over the entire surface of the magnetic recording medium. If foreign matter or scratch is present on the magnetic recording medium 212, the laser beam is scattered. By receiving the scattering light by the observing optical system 224, presence of foreign matter, size, kind and so forth can be recognized.

When inspection is completed, the inspected magnetic recording medium 212 is transported to the transfer index 214 by the arm 215 of the handler 216 through the operation opposite to the foregoing. At this time, when the arm 215 is rotated in the same direction as transporting the magnetic recording medium 212 to the inspection spindle 218 (when inspection is not performed continuously, it is possible to rotate in reverse direction). Furthermore, the transfer index 214 transfers the inspected magnetic recording medium 212 to the lifter 210. The lifter 210 lowers the magnetic recording medium 212 to house the magnetic recording medium 212 in the cassette 204.

When the inspection operation is performed continuously, the handler 216 of the optical type inspection apparatus of the present invention may have a plurality of arms, for example two arms 215 as set forth above, the transporting operation of the magnetic recording medium 212 to the inspection spindle 218 and operation for collecting the magnetic recording medium 212 within the cassette can be performed simultaneously. In this case, a plurality of arms (for example two arms) rotates in the same direction.

It should be noted that the magnetic recording medium 212 is neatly nested with orienting in the predetermined direction so that light is irradiated on the surface side to be inspected.

Next, the third aspect of the present invention will be described.

The third aspect of the present invention is directed to the magnetic recording medium transferred the servo signal by the foregoing first aspect of the magnetic transfer apparatus.

At first, the magnetic recording medium will be described.

The magnetic recording medium of the present invention is same as the magnetic recording medium used in the conventional apparatus for writing the servo signal by the conventional magnetic head.

Figure 6:
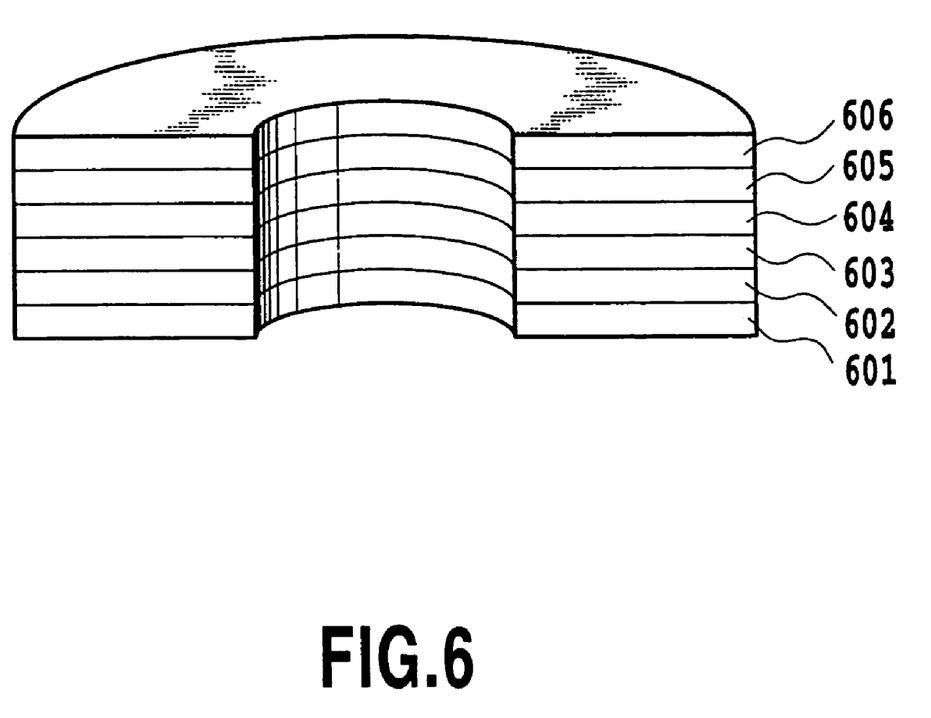
FIG. 6 is a fragmentary section of a magnetic recording medium.

Hereinafter, description will be given for the magnetic recording medium not written the servo signal (hereinafter simply referred to as magnetic recording medium). The magnetic recording medium of the present invention is shown in FIG. 6, for example. Particular structure is as follow.

As shown in FIG. 6, the magnetic recording medium has a substrate 601, a plating layer 602, a non-magnetic undercoat layer 603, a magnetic layer 604, a protective layer 605 and a liquid lubricating layer 606 formed in sequential order.

As the substrate 601, a blank material of aluminum alloy is used. Ni—P plating is applied to the substrate as the plating layer 602. In the present invention, a glass substrate, a plastic substrate (e.g. polyolefin, polycarbonate, polyacrylate, norbornene resin and the like) and the like may also be used as the substrate. An example of the glass substrate may be aluminum silicate glass, soda limb glass or the like.

Hereinafter, the magnetic recording medium will be explained with taking the most common aluminum alloy as an example of the substrate.

As set forth above, Ni—P plating (plating layer 602) is applied to the aluminum alloy substrate. Then, the non-magnetic undercoat layer 603, the magnetic layer 604, the protective layer 605 and the liquid lubricant layer 606 are formed in sequential order to make the magnetic recording medium. The non-magnetic undercoat layer 603, the magnetic layer 604, the protective layer 605 and the liquid lubricant layer 606 are formed with the conventionally known materials. Particularly, the non-magnetic undercoat layer 603 is an undercoat layer comprising Cr, for example. The magnetic layer 604 is comprised of Co alloy, for example Co—Cr—Pt, Co—Cr—Ta and the like as ferromagnetic alloy. The protective layer 605 is a carbon protective layer or the like, for example. Furthermore, the liquid lubricant layer 606 is a fluorinated lubricant or the like, such as perfluoropolyether lubricants.

While the magnetic recording medium according to the present invention has been explained with reference to FIG. 6, the shown structure is mere example and can be modified in various ways depending upon application of the magnetic recording medium. Also, the shape of the magnetic recording medium may be adapted to the equipment using the magnetic recording medium according to the present invention, and not particularly specified. For example, in case of the magnetic recording medium to be used in the hard disk drive (HDD), the magnetic recording medium may be a disc shaped magnetic recording medium.

The magnetic recording medium according to the present invention is a magnetic recording medium produced by magnetically transferring servo signal by the first aspect of the magnetic transfer apparatus on a blank magnetic recording medium not transferred data. For example, the magnetic recording medium is one illustrated in FIG. 5.

Next, the fourth aspect of the present invention, namely a production method of the magnetic recording medium, will be explained.

The method for manufacturing the magnetic recording medium according to the present invention comprises steps of forming at least the magnetic layer, the protective layer and the liquid lubricant layer on the substrate for magnetic recording medium produced by providing Ni—P plating as plating layer on aluminum alloy material.

More specifically, the method for manufacturing the magnetic recording medium according to the present invention comprises a step of obtaining the substrate for the magnetic recording medium and steps of forming at least the magnetic layer, the protective layer and the liquid lubricant layer on the substrate.

The substrate for the magnetic recording medium can be produced in the following manner.

A blank material of the aluminum alloy can be used as the substrate 601. As other materials of the substrate 601, a glass substrate, a plastic substrate (e.g. polyolefin, polycarbonate, polyacrylate, norbornene resin and the like) and the like may also be used. As the glass substrate, chemically reinforced glass substrate or the like may be used. Examples of the glass substrate include aluminum silicate glass, soda limb glass or the like.

Hereinafter, a process for the manufacturing the magnetic recording medium will be described with taking the most common aluminum alloy as an example of the substrate Blank material of aluminum alloy is one normally used for hard disk or the like. For example, in the present invention, the blank material of aluminum alloy can be used which obtained by rolling and annealing the aluminum alloy material molten by heating and processing the resultant aluminum alloy into a predetermined dimension. Next, for improving surface precision, surface polishing of the blank material of aluminum alloy is performed and thereafter Ni—P plating (plating layer) is provided. Plating is performed by electroless plating. A thickness of Ni—P plating is not specified as long as applicable thickness for normal magnetic recording medium, and can be about 13 m, for example.

For the substrate for magnetic recording medium (hereinafter referred to as substrate including the plating layer 602), a polish processing and a texture processing (polish-texture processing) are applied, and surface is polished.

Polish-texture processing is performed by polishing of the surface of the substrate for magnetic recording medium to achieve the surface roughness of Ra=1 nm (10 Å). Next, by a texture processing using the diamond slurry, substantially concentric grooves are formed so that the surface of the magnetic recording medium has a surface roughness of, for example, Ra=30 Å.

Next, obtained substrate is washed. Washing method is not specified as long as normally used for washing the substrate for magnetic recording medium. For example, any of a dipping method, dipping and vibrating method, spraying method and so forth may be used for washing. On the other hand, the washing period of time is different by washing means, but it is preferably 1 to 3 minutes.

Next, laser zone texture (LZT) process is performed on the substrate. The LZT process can be performed by a method known in the field of magnetic recording medium. For example, laser zone texture process is applied by laser, so that bumps of a predetermined height and predetermined radius (e.g. BH=23 nm and BD=7 $\mu$m) are formed in Contact Start Stop (CSS) zone of the substrate.

On the upper surface of the substrate, the layer structure enabling magnetic recording is laminated. In lamination process, the non-magnetic undercoat layer 603 is coated on the substrate for magnetic recording medium. On the non-magnetic undercoat layer, the magnetic layer 604 and the protective layer 605 are formed in sequential order. Subsequently, lubricant diluted by solvent is applied on the surface of the protective layer 605.

In the present invention, the non-magnetic undercoat layer 603 and the magnetic layer 604 may be formed of materials generally used in the field of magnetic recording medium. For example, as the non-magnetic layer, Cr layer may be used. On the other hand, as the magnetic layer 604, Co—Cr—Pt alloy layer may be used.

When the non-magnetic undercoat layer 603, the magnetic layer 604 and the protective layer 605 are respectively Cr non-magnetic undercoat layer, Co—Cr—Pt ferromagnetic alloy layer and carbon protective layer, those layers may be formed by sputtering. On the other hand, when the protective layer 605 is carbon protective layer, it may be the carbon protective layer taking normal graphite as primary component or Diamond Like Carbon (DLC) protective layer. On the other hand, the lubricant layer 606 can be applied by dip coat method, spin coat method and so forth.

The thickness of the non-magnetic undercoat layer 603, the magnetic layer 604, the protective layer 605 and the lubricant layer 605 are the thickness normally used in the magnetic recording medium. It should be noted that the layer structure is not limited to those set forth above.

For the magnetic recording medium obtained through the process set forth above, the servo signal is written by the magnetic transfer apparatus described in connection with the first aspect of the invention. Writing of the servo signal is as set forth in connection with the first aspect of the invention.

The surface condition of the magnetic recording medium according to the present invention can be inspected by means of the optical type inspection apparatus described in connection with the second aspect of the present invention.

EXAMPLES

Hereinafter, the present invention will be described in more detail with the following preferred embodiment.

<Analysis of Greasing Agent>

Concerning greasing agent used in the magnetic transfer apparatus or the optical type inspection apparatus, analysis is performed in the following manner.

In the shown embodiment, a plurality of greases for clean environment is taken for analysis. Particularly, the following greases are used:

1) AFB grease available from THK Kabushiki Kaisha
2) AFE grease available from THK Kabushiki Kaisha

Analysis was performed by GC-MASS device. Analyzing procedure is as follows:

1) Grease sample was applied to an aluminum strip of 5×65 mm.
2) The aluminum strip was put in a test tube and was heated at 100° C. for 10 minutes under flow of 12 sccm of helium. Gas generated from the heated grease was trapped and condensed. After condensation, analysis was performed by GC-MASS device (QP5000 from Kabushiki Kaisha Shimadzu Seisakusho).
3) Analysis condition is as follows:

Analyzing Column: NB5 Column from CL Science Kabushiki Kaisha (length of 30 m, outer diameter of 0.25 mm and inner diameter of 0.4 $\mu$m)
Column Vessel Initial Temperature: 40° C.
Vaporizing Chamber Temperature: 280° C.
Interface Temperature: 280° C.

Column Vessel Temperature Condition during Analysis:
Temperature was elevated from 40° C. to 280° C. at a rate of 10° C./minute.

Result of analysis will be shown in the case where AFB grease (hereinafter referred to as grease A) is used. FIG. 7 shows a result of analysis by GC. In the drawings, 701 to 705 show peaks of sulfur type gas generated in this test. Particularly, bis(2-methyl-2-propenyl)sulfide (701: $C_8H_{14}S$, molecular weight: 142), methylthiirane (702; $C_3H_6S$, molecular weight 74), 3,5-bis(1-methylethyl)-1,2,4-trithiolane (703 and 704; $C_8H_{16}S_3$, molecular weight: 208), S-propyl octanethioate (705, $C_{11}H_{22}OS$, molecular weight: 202) and the like may be listed. Chemical formula of these compounds is as follows:

Each concentration of these five compounds was calculated using 2-propenyloxybenzene ($C_6H_5OCH_2CH=CH_2$) as standard material of calibration curve.

In case of grease used in the shown embodiment, the total concentration of the five compounds was 5.85 ppb.

On the other hand, result of analysis in the case where AFE grease as another grease (hereinafter referred to as grease B) was used as analyzing sample is shown in FIG. 8.

In FIG. 8, 801 is S-propyl octanethioate. Concentration of this compound was 0.35 ppb.

Magnetic Recording Medium

Magnetic transfer for the magnetic recording medium using the magnetic transfer apparatus using the foregoing two kinds of greases was performed.

As the magnetic recording medium, the magnetic recording medium was provided, which Cr non-magnetic undercoat layer (10 nm thick), the magnetic recording layer formed of Co—Cr—Pt alloy (30 nm thick), the protective layer of carbon (10 nm thick) and the liquid lubricant layer of perfluoroether lubricant (1 nm thick) were layered on the aluminum alloy substrate applied Ni—P plating. On the surface of silicon substrate of 500 m thick, magnetic material (500 nm thick) was applied to form a pattern corresponding to the desired servo signal thereby to make the master disk. The pattern of the magnetic material was provided in a line form regions extending in radius direction were provided as shown in FIG. 4.

At first, a vertical uniform magnetic field of a strength of 0.5 T is applied to the surface of the magnetic recording medium using the external magnet for uniformly orienting the magnetization of the magnetic recording layer of the magnetic recording medium to initialize the magnetic recording medium.

Next, the master disk was tightly fitted on one surface of the initialized magnetic recording medium. The master disk was fitted to the magnetic recording medium so that the surface of the master disk where the magnetic material was patterned faces toward the magnetic recording medium, thereby to form a laminate. From the side of the master disk in the laminate, magnetic field (0.5 T) was applied in opposite direction as magnetic erasure. Application of magnetic field was performed by rotating the external magnet in one turn along the surface of the master disk.

Magnetic Recording Medium Test

The obtained magnetic recording medium was left in high temperature and high humidity environment of 60° C. and 80% of relative humidity for 10 hours to measure corrosion of the surface of the magnetic recording medium. Measurement was performed for one hundred of magnetic recording media which were from the three thousandth of magnetic recording medium after beginning the use of the new grease to the three thousand one hundredth.

As a result, with the grease B (total concentration of sulfur type gas at 0.35 ppb), corrosion was not observed at all. With the grease A (total concentration of sulfur type gas at 5.85 ppb) corrosion was observed in two of one hundred magnetic storage media.

On the other hand, similar test was performed with respect to the optical type inspection apparatus to obtain similar result.

From the foregoing result, grease used in the magnetic transfer apparatus and the optical type inspection apparatus, it is desirable that total concentration of sulfur type gas analyzed by the foregoing analyzing method is less than or equal to 0.5 ppb, and more preferably 0.35 ppb.

The present invention has been described in detail with respect to preferred embodiments, and it will now be apparent from the foregoing to those skilled in the art that changes and modifications may be made without departing from the invention in its broader aspects, and it is the intention, therefore, in the appended claims to cover all such changes and modifications as fall within the true spirit of the invention.

What is claimed is:

1. An optical type inspection apparatus for optically inspecting scratch or foreign matter on a magnetic recording medium, comprising:
    an optical system for irradiating a light on said magnetic recording medium to inspect a surface of said magnetic recording medium;
    an automatic focusing shaft for focusing said optical system;
    a transporting portion for transporting said magnetic recording medium to said optical system;
    wherein the optical type inspection apparatus has a plurality of movable portions using grease
    wherein total amounts of a sulfur type gas generated from said plurality of the movable portions is less than or equal to 0.5 ppb.

2. The optical type inspection apparatus as claimed in claim 1, wherein the total amount of sulfur type gas is less than or equal to 0.35 ppb.

* * * * *

UNITED STATES PATENT AND TRADEMARK OFFICE
CERTIFICATE OF CORRECTION

PATENT NO. : 7,012,681 B2
APPLICATION NO. : 10/845155
DATED : March 14, 2006
INVENTOR(S) : Kondo et al.

It is certified that error appears in the above-identified patent and that said Letters Patent is hereby corrected as shown below:

<u>On title page Item (73)</u>:

The Assignee, "Fuji Electric Co., Ltd., Kanagawa, Japan" should be --Fuji Electric Device Technology Co., Ltd., Tokyo, Japan--.

Signed and Sealed this

Seventh Day of August, 2007

JON W. DUDAS
*Director of the United States Patent and Trademark Office*